United States Patent [19]

Humphries et al.

[11] Patent Number: 4,741,619
[45] Date of Patent: May 3, 1988

[54] HYDROPHILIC MICROPLATES FOR VERTICAL BEAM PHOTOMETRY

[75] Inventors: Gillian M. K. Humphries, Los Altos; Viola T. Kung, Menlo Park, both of Calif.

[73] Assignee: Molecular Devices Corporation, Palo Alto, Calif.

[21] Appl. No.: 47,037

[22] Filed: May 5, 1987

[51] Int. Cl.⁴ .............................................. G01N 21/03
[52] U.S. Cl. .................................. 356/246; 356/440; 422/102
[58] Field of Search .............. 356/246, 440; 250/526; 422/102

[56] References Cited

U.S. PATENT DOCUMENTS

| 3,992,150 | 11/1976 | Retzer | 356/246 X |
| 4,254,223 | 3/1981 | Schuurs et al. | 356/246 X |
| 4,319,841 | 3/1982 | Suovaniemi et al. | 356/246 X |
| 4,599,315 | 7/1986 | Terasaki et al. | 356/246 X |

FOREIGN PATENT DOCUMENTS 135303 3/1985 European Pat. Off. ............ 356/246

Primary Examiner—Davis L. Willis
Assistant Examiner—Matthew W. Koren
Attorney, Agent, or Firm—Leydig, Voit & Mayer

[57] ABSTRACT

A microtiter plate prepared from a hydrophobic plastic is rendered more hydrophilic by treatment of the surfaces of the wells of the microplate prior to use. The resulting plates are particularly useful in vertical beam photometry.

14 Claims, 1 Drawing Sheet

HYDROPHILIC MICROPLATES FOR VERTICAL BEAM PHOTOMETRY

BACKGROUND OF THE INVENTION

1. Field of the Invention

This invention is directed to sample holders utilized in vertical beam photometers and to techniques for improving the reliability of assays conducted using such sample holders.

2. Description of the Background

Microplates, which are molded plastic plates having a number of small depressions known as wells in which individual reactions can be carried out, are useful in a wide variety of chemical and biochemical applications in which a number of related procedures are carried out at the same time. Originally, photometry on the contents of such microplates was accomplished by withdrawing samples from the wells and conducting an assay in a different location (e.g., in the cuvette of a spectrophotometer) to determine the content of each individual well. More recently, the technique of vertical beam photometry has been utilized to conduct a direct assay in the individual wells. The microplate is placed in a carrier which operates to automatically position the plate so that a vertical beam of light sequentially passes through the individual wells. Absorbance of the light is measured in the manner typical for photometry, thereby giving a direct reading of the absorbance in each well, which can be related to the presence and amount of numerous light-absorbing substances.

Apparatuses for conducting vertical beam photometry are available commercially and have been utilized in numerous assays, such as enzyme-linked immunosorbent assays. However, there remains room for improvement in the microplates utilized in such assays, particularly improvements related to the reliability and reproducibility of measurements.

SUMMARY OF THE INVENTION

The present invention provides a microplate having hydrophilic well walls, thereby providing conditions which result in improved reliability of optical density measurements using vertical beam photometers. Surfactant-coated well walls are particularly preferred.

BRIEF DESCRIPTION OF THE DRAWING

The present invention will be better understood by reference to the following detailed description when considered in combination with the accompanying drawing which forms part of the present specification, wherein:

The FIGURE is a vertical cross-section of a microplate showing four wells, the two left wells being untreated and the two right wells being treated to render them more hydrophilic.

DESCRIPTION OF SPECIFIC EMBODIMENTS

Figure 1:
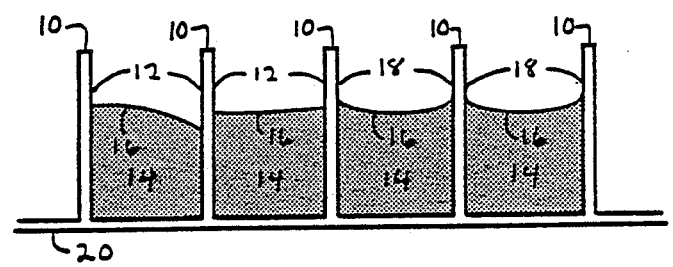

The present invention arose with the realization that the precision and reliability of both endpoint and kinetic optical density (OD) measurements utilizing vertical beam photometers could be improved by modifying the walls of microplate wells to render them hydrophilic rather than hydrophobic. Polystyrene and other materials commonly used in making microplates are relatively hydrophobic and are generally not wetted by the solutions present in the wells that are being measured. By rendering the walls of the wells hydrophilic, a planar horizontal meniscus is obtained (in the center of the wells) that is perpendicular to the vertical beam of light used in the vertical beam photometer. The meniscus is gravity-controlled and remains perpendicular to the beam of light even if the plate is slightly tilted. By providing a hydrophilic well wall, the vertical path length through the center of each hydrophilic well will be the same when the plate is placed in a vertical beam photometer as long as the geometry of the wells and the volumes of the solutions in each well are identical.

The problem and its solution are readily apparent from consideration of the FIGURE, which is a vertical cross-section showing four adjacent sample wells of a microplate. The wells are formed by vertical walls 10 attached to base plate 20. On the left-hand side of the figure are two hydrophobic wells that have not been treated by the process of the present invention. Accordingly, inner walls 12 are hydrophobic. Liquid sample 14 therefore makes poor contact with well walls 12, resulting in a meniscus 16 that varies from well to well. The meniscus may be tilted unevenly to one side, as shown in the first well, or flat, as shown in the second well. The response of the meniscus to gravity is slow and erratic because the aqueous sample does not wet the well surfaces evenly. Accordingly, unequal vertical pathlengths arise in the wells which, even with wells of identical geometry and equal sample volumes, leads to poor precision in optical density measurement with a vertical beam photometer.

The two wells on the right-hand side of the figure represent wells treated by the process of the present invention. When well walls 18 are rendered hydrophilic, sample 14 evenly contacts all of the walls, and meniscus 16 is identical from well to well, as shown in the two right-hand wells. Thus, as long as the geometry of the wells and the volumes of sample in each well are identical, the vertical pathlength through the center of each hydrophilic well will be the same when the microplate is placed in a vertical beam photometer.

The terms hydrophilic and hydrophobic are by their very nature relative terms. Improvement in reliability is seen with increasing hydrophilic character of the well walls, so that the present invention can be practiced by utilizing any technique that will increase the hydrophilic nature of the well surface. However, certain advantages are achieved when the hydrophilic character of the surface reaches specific levels.

The absolute hydrophilic or hydrophobic character of a surface can be measured by an index known as wetting angle. The wetting angle is defined to be the angle of intersection between a horizontal surface and a plane incident to the surface of a drop of fluid placed on the surface. When measuring hydrophilicity, the liquid utilized is water. If the surface is completely wettable with water, it tends to spread out into a thin layer so as to have a very small wetting angle approaching zero. If the surface is completely hydrophobic so that no wetting of the surface occurs, a drop of water (having a volume of about 30 $\mu$) sits as a flattened sphere on the surface, thereby providing a wetting angle approaching 180°. In the practice of the present invention, the preferred wetting angle is less than 3°, more preferably less than 1°.

Any technique that will increase the hydrophilic nature of the well surface to the level described above can be utilized to prepare a microplate of the invention. Examples include plasma etching and corona discharge treatments as well as coating the surfaces with an amphophilic or hydrophilic substance. For example, the surfaces can be immersed in a solution containing a surfactant (i.e, an amphophilic substance). The structure of the surfactant is not essential to the practice of the invention as long as the surfactant is capable of increasing the hydrophilic nature of the well surfaces. Whether a given surfactant is suitable for practice with the present invention can readily be determined by simple experimentation, for example by preparing a solution (or suspension) containing from about 0.005 to about 0.1% of the surfactant and immersing a surface of the type to be treated in the solution. The wetting angle can then be measured, if necessary, to determine the specific hydrophilic character of the surface.

All of the following types of surfactants can be utilized in the present invention: (a) soaps (i.e., alkali salts) of fatty acids, rosin acids, and tall oil: (b) alkyl arene sulfonates; (c) alkyl sulfates, including surfactants with both branched-chain and straight-chain hydrophobic groups, as well as primary and secondary sulfate groups: (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters, (f) polyethylene glycol ethers of alkylphenols; (g) polyethylene glycol ethers of long-chain alcohols and mercaptans; (h) fatty acyl diethanol amides; and (i) block copolymers of ethylene oxide and propylene oxide.

A number of surfactants are particularly useful for biochemical reactions and are marketed as such by chemical and biochemical supply houses. For example, a number of biological detergents (surfactants) are listed as such by Sigma Chemical Company on pages 310–316 of its 1987 catalog of biochemical and organic compounds. Such surfactants are divided into four basic types: anionic, cationic, zwitterionic, and nonionic. Examples of anionic detergents include alginic acid, caprylic acid, cholic acid, 1-decanesulfonic acid, deoxycholic acid, 1-dodecanesulfonic acid, N-lauroylsarcosine, and taurocholic acid. Cationic detergents include dodecyltrimethylammonium bromide, benzalkonium chloride, benzyldimethylhexadecyl ammonium chloride, cetylpyridinium chloride, methylbenzethonium chloride, and 4-picoline dodecyl sulfate. Examples of zwitterionic detergents include 3-[(3-cholamidopropyl)-dimethylammonio]-1-propanesulfonate (commonly abbreviated CHAPS), 3-[(cholamidopropyl)-dimethylammonio]-2- hydroxy-1 -propanesulfonate (generally abbreviated CHAPSO), N-dodecyl-N,N-dimethyl-3-ammonio-1-propanesulfonate, and lyso-$\alpha$-phosphatidylcholine. Examples of nonionic detergents, which comprise a preferred class of biological detergents, include decanoyl-N-methylglucamide, diethylene glycol monopentyl ether, n-dodecyl $\beta$-D-glucopyranoside, ethylene oxide condensates of fatty alcohols (e.g., sold under the trade name Lubrol), polyoxyethylene ethers of fatty acids (particularly $C_{12}$–$C_{20}$ fatty acids), polyoxyethylene sorbitan fatty acid ethers (e.g., sold under the trade name Tween), and sorbitan fatty acid ethers (e.g., sold under the trade name Span). Polyoxyethylene fatty acid esters and polyoxyethylene sorbitan fatty acid esters are particularly preferred surfactants. Mixtures of surfactants are also useful.

The amount of surfactant applied to the surface can be quite small while still effectively increasing the hydrophilic character of the surface. For example, amounts of surfactant in the range of from about 0.01 to about 1 $\mu g/cm^2$ are sufficient for about 0.01 increasing the hydrophilic character of a surface.

The technique by which the surfactant is applied to the surface is not a material part of the overall invention although certain advantages can be achieved in the manufacturing process by matching particular techniques for application with individual surfactants, as will be apparent to those of ordinary skill in the art. Suitable techniques for treating surfaces include immersing the surface in a solution containing the surfactant or spraying a solution or suspension of the surfactant on the surface. These steps would typically be followed by drying to remove the solvent, which can be either water or an organic solvent with a low boiling point, preferably less than 80° C., in which the surfactant is either soluble or in which it can be suspended. Many variations can be carried out, such as immersing a surface to be treated in a concentrated solution of the surfactant followed by washing to remove excess surfactant and drying to remove the solvent used in washing.

It is also possible to use the techniques of plasma etching and corona discharge to render hydrophobic surfaces more hydrophilic. Typical conditions are use of argon plasma in a one torr pressure chamber for 5 to 10 minutes at 10 to 25 watts of energy at 13.56 MHz. See, for example, U.S. Pat. No. 3,376,208 (Electric Discharge to Modify a Film Surface). Such treatments can be restricted to the walls of the wells of the microplate, but treatment of the entire plate, including surfaces that are not to be wetted, does not adversely affect the present invention.

The manufacturing process for preparing microplates need not be changed by the process of the present invention other than to include a step of treating the well walls to make them more hydrophilic. Typically, plates will be manufactured by standard techniques and the well walls rendered hydrophilic after the manufacturing process is essentially complete. However, it is also possible to carry out the process of the present invention at an earlier stage of manufacture, including construction from a material which is itself sufficiently hydrophilic to permit adequate wetting. To the extent that manufacturing includes final processing of the microplates and their preparation and shipment to the user, any activity by the manufacturer that occurs before shipment is considered to occur during manufacture. It is preferred to treat the wells of the microplates during the manufacturing process rather than to have them treated by the ultimate user at the point of use, although such later treatment will also create a microplate of the invention.

It is recognized that certain prior art techniques, such as ELISA techniques using microplates, use detergents in one or more steps of the process to remove nonspecifically bound proteins or other molecules. Final OD readings in such microplates are carried out in sample wells in which the walls may be coated with a hydrophilic detergent used during one or more of such wash steps. However, there does not appear to have been any recognition of the problem set forth in this specification, nor of its solution. Furthermore, techniques used in ELISA assays use detergents in various wash steps that occur after the aqueous sample or reagent has been added to the wells. The surfaces of wells are treated prior to the addition of aqueous sample or reagent in a process of the present invention and in the production of microplates of the present invention.

The invention now being generally described, the same will be better understood by reference to the following examples which are provided for purposes of illustration only and are not to be considered limiting of the invention unless so specified.

EXAMPLE

Standard polystyrene microplates with 300 μl wells, obtained from Dynatech, Falcon, Costar, and Nunc, were treated to make the well walls more hydrophilic by filling the wells with a solution containing 0.01% Tween-20 in a buffer consisting of 0.15M NaCl with 0.01M phosphate, pH 7.0. The microplate containing the surfactant solution was allowed to stand for one hour before being emptied and dried in air.

The change in hydrophilic nature of the plates was visible to the naked eye upon addition of aqueous solution to the wells. When 150 μl of a dye solution was added to each well, the side walls of the wells that were treated with the surfactant were wetted. Even when the plate was tilted, its meniscus moved in a gravity-controlled manner with the center being essentially planar and parallel to the horizon. When the same dye solution was added to a standard polystyrene microtiter plate that had not been so treated, the meniscus was flat in some cases but in other cases was tilted unevenly to one side. When the microplate was tilted, the response of the fluid in each well to gravity was slow and erratic. These visible differences were substantiated by quantitative measurements to determine the precision of measurements that could be obtained with either untreated or treated microplates.

Tables 1 and 2 below report data obtained using the Vmax Kinetic Microplate Reader from Molecular Devices, Palo Alto, CA, for endpoint and kinetic OD readings. The tables illustrate an increase in precision obtained using hydrophilic microplates. For endpoint OD measurements, the Vmax performance was compared with that of a Biotek EL310 (endpoint only) ELISA Microplate Reader (data not shown). Both instruments similarly detect the increase in precision observed with hydrophilic plates.

TABLE 1

Precision of End-Point Assays Measured by Vertical Beam Photometry

| Tween-20 Treated | | | Without Treatment | | |
|---|---|---|---|---|---|
| Final OD* | Std. Dev. | CV (%) | Final OD* | Std. Dev. | CV (%) |
| 0.804 | 0.0032 | 0.40 | 0.848 | 0.0105 | 1.24 |
| 0.805 | 0.0039 | 0.48 | 0.835 | 0.0080 | 0.96 |
| 0.803 | 0.0038 | 0.47 | 0.835 | 0.0076 | 0.91 |
| 0.805 | 0.0044 | 0.55 | 0.831 | 0.0087 | 1.05 |
| 0.808 | 0.0033 | 0.41 | 0.795 | 0.0086 | 1.08 |
| 0.798 | 0.0049 | 0.61 | 0.811 | 0.0096 | 1.18 |
| 0.786 | 0.0034 | 0.43 | 0.780 | 0.0087 | 1.12 |
| 0.807 | 0.0045 | 0.56 | 0.819 | 0.0102 | 1.24 |
| | Mean CV: | 0.49 | | Mean CV: | 1.10 |

*Each final OD is the mean of six readings.

The data above was obtained reading individual wells of a flat-bottomed microplate six times each, reversing the position of the microplate between each reading. For example, well A01 was first read in position A01 of the Vmax, then in position H12 of the Vmax, with these two steps being repeated three times. The mean, standard deviation (SD), and percent coefficient of variation (CV) for the six optical density (OD) values read for each well were then calculated. The experiment was performed at 650 nm, using a blue dye solution (150 μl well). Results from two columns of eight individual wells are shown. One of the columns was pretreated with a buffer solution containing Tween 20 to make the well surfaces hydrophilic as described. The other column was not pretreated. These data are representative of repetitions of this experiment.

The coefficients of variation obtained on repeat readings of individual wells are approximately halved by pretreatment with Tween in this experiment. Note that the mean OD values are lower when the microplate has been Tween-treated, because the geometry of the meniscus shortens the pathlength.

TABLE 2

Precision of Kinetic Assays Measured by Vertical Beam Photometry

| Tween-20 Treated | | | Without Treatment | | |
|---|---|---|---|---|---|
| Rate (mOD min) | Std. Dev. | CV (%) | Rate (mOD/min) | Std. Dev. | CV (%) |
| 181.5 | 3.8 | 2.1 | 207.4 | 10.7 | 5.2 |
| 98.8 | 1.3 | 1.3 | 109.4 | 2.6 | 2.4 |
| 78.8 | 1.6 | 2.0 | 87.0 | 2.7 | 3.1 |
| 64.3 | 1.2 | 1.9 | 70.6 | 2.5 | 3.5 |
| 36.4 | 0.5 | 1.4 | 39.3 | 0.75 | 1.9 |
| | Mean CV: | 1.7 | | Mean CV: | 3.2 |

Table 2 shows kinetic data generated by fluid-phase alkaline phosphatase with p-nitrophenylphosphate as substrate in a microplate having columns 1-5 (eight wells per column) pretreated to make the wells hydrophilic. Columns 7-11 were not treated. The mean values shown are computed from rates exhibited by eight wells containing equal enzyme activities (in as far as pipetting accuracy would allow). Measurements were made at 405 nm, with AUTOMIX turned off, for a total read time of 2 minutes. This meant that data points were gathered for each well every five seconds. For fluid-phase, enzyme-mediated reactions, the increase in precision gained by making the plate hydrophilic is similar when AUTOMIX is turned on.

All publication and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for improving the precision of optical density measurements made utilizing a vertical beam photometer to determine the presence or amount of analyte in the wells of a microplate, which comprises:
    treating the surfaces of the wells of said microplate in order to increase the hydrophilic character of said surfaces prior to adding aqueous sample or reagent to said wells.

2. The method of claim 1, wherein treating comprises coating said surfaces with a surfactant.

3. The method of claim 2, wherein said surfactant is selected from the group consisting of polyoxyethylene sorbitan fatty acid esters and polyoxyethylene fatty acid esters.

4. The method of claim 2, wherein said surfactant is applied to said surface at the rate of from 0.01 to 1 $\mu g/cm^2$.

5. The method of claim 1, wherein treating said surfaces comprises subjecting said surfaces to an electric discharge.

6. The method of claim 1, wherein treating said surfaces comprises covalent attachment of hydrophilic chemical moieties.

7. The method of claim 1, wherein said treating occurs during the process of manufacturing said microplate.

8. A microplate for use in vertical beam photometry, wherein the surfaces of the wells of said microplate comprise a hydrophobic plastic treated to increase hydrophilicity beyond that which is present for said hydrophobic plastic when untreated.

9. The microplate of claim 8, wherein said plastic comprises polystyrene or a copolymer containing styrene monomers.

10. The microplate of claim 9, wherein said polystyrene is coated with a surfactant.

11. The microplate of claim 10, wherein said surfactant is selected from the group consisting of polyoxyethylene fatty acid esters and polyoxyethylene sorbitan fatty acid esters.

12. The microplate of claim 8, wherein said surfaces have been subjected to corona discharge or plasma etching.

13. The microplate of claim 8, wherein said surfaces are modified by covalent attachment of hydrophilic chemical moieties.

14. The microplate of claim 8, wherein the wetting angle for water on said treated surfaces is less than 3°.

* * * * *